United States Patent
Bae et al.

(10) Patent No.: US 8,103,336 B2
(45) Date of Patent: Jan. 24, 2012

(54) APPARATUS, MEDIUM, AND METHOD FOR MEASURING BODY FAT

(75) Inventors: Sang-kon Bae, Seoul (KR); Woo-young Jang, Seoul (KR)

(73) Assignee: Samsung Electronics Co., Ltd.

( * ) Notice: Subject to any disclaimer, the term of this patent is extended or adjusted under 35 U.S.C. 154(b) by 869 days.

(21) Appl. No.: 11/253,653

(22) Filed: Oct. 20, 2005

(65) Prior Publication Data

US 2006/0100532 A1     May 11, 2006

(30) Foreign Application Priority Data

Nov. 8, 2004    (KR) .................. 10-2004-0090349

(51) Int. Cl.
*A61B 5/05*     (2006.01)
*A61B 5/103*    (2006.01)
*A61B 5/117*    (2006.01)
*G01N 33/48*    (2006.01)
*G01N 33/50*    (2006.01)

(52) U.S. Cl. .......... 600/547; 600/587; 702/19; 702/159; 702/172

(58) Field of Classification Search .......... 600/547, 600/587; 702/19, 155, 158, 159, 170, 172
See application file for complete search history.

(56) References Cited

U.S. PATENT DOCUMENTS 3,719,928 A  *  3/1973   Oishi et al. ............... 340/870.03
4,808,948 A  *  2/1989   Patel et al. ........................ 331/4
6,005,398 A  *  12/1999  Landt ............................. 324/650
2002/0183645 A1 * 12/2002 Nachaliel ...................... 600/547
2004/0077969 A1 *  4/2004 Onda et al. .................... 600/547

FOREIGN PATENT DOCUMENTS

JP           11309123 A  * 11/1999
JP         2000139865 A  *  5/2000

OTHER PUBLICATIONS

Machine translation of JP 2000-139865A. Japanese Patent Office. pp. 1-7.*
Machine translation of JP 11-309123A. Japanese Patent Office. pp. 1-7.*
Machine translation of JP 11-309123A. Japanese Patent Office. Translation produced Jul. 30, 2009 based on document published Nov. 1999. pp. 1-7.*
Machine translation of JP 2000-139865A. Japanese Patent Office. Translation produced Jul. 30, 2009 based on document published May 2000. pp. 1-7.*

* cited by examiner

*Primary Examiner* — Max Hindenburg
*Assistant Examiner* — John Pani
(74) *Attorney, Agent, or Firm* — Staas & Halsey LLP

(57) ABSTRACT

An apparatus, medium, and method for measuring body fat. The apparatus may include a current generating unit generating a current having a predetermined range of variable frequency and applying the current to a desired area in a human body to be measured, a detector unit detecting a voltage generated from the desired area in response to the current having a variable frequency and detecting a frequency value at which impedance of the desired area is changed based on relation between the detected voltage and the variable frequency, and a body fat calculating unit calculating body fat thickness based on the detected frequency value. It is possible to measure body fat thickness in any part of a human body by applying a variable frequency current to a desired area. Therefore, health and fatness management can be accomplished for each part of a human body.

10 Claims, 13 Drawing Sheets

APPARATUS, MEDIUM, AND METHOD FOR MEASURING BODY FAT

CROSS-REFERENCE TO RELATED APPLICATIONS

This application claims the priority benefit of Korean Patent Application No. 10-2004-0090349, filed on Nov. 8, 2004, in the Korean Intellectual Property Office, the disclosure of which is incorporated herein in its entirety by reference.

BACKGROUND OF THE INVENTION

1. Field of the Invention

Embodiments of the present invention relate to an apparatus, medium, and method for measuring body fat, and more particularly, to an apparatus, medium, and method for measuring body fat, where body fat thickness is measured in a desired area of a body by applying a variable frequency current to the desired area.

2. Description of the Related Art

A body, e.g., a human body, may be made up of mainly four elements, including water, protein, fat, and inorganic matter. A proportion of the elements may be different depending on an individual's heath conditions such as sex or weight, but can be approximated to respective proportions of 55:20:20:5. It is known that the proportion of the four human body elements can be identified by measuring body water amount. This is because the protein and the body water are main elements of human muscle and they are proportional to one another. Specifically, healthy muscle contains 70% water and 27% protein. The inorganic matter in a human body includes the weight of the bones, and the weight of the bones is closely associated with muscle amount. In short, protein and inorganic matter amounts in a human body can be obtained from the body water amount, and thus the body fat amount can be calculated by subtracting the sum of the body water, protein, and inorganic matter amounts from the total weight. Currently, the most frequently used method of measuring body fat is a bioelectrical impedance analysis (BIA), with there being a lot of other methods, such as an analysis of body density in water, computed tomography (CT), and a measurement of subcutaneous fat thickness.

The bioelectrical impedance analysis method employs the fact that the body water amount is inversely proportional to the bioelectrical impedance. This method is advantageously fast, simple, and non-invasive. If a weak alternating current (AC) electrical signal is applied to a human body, it would flow through body water having a high electrical conductivity. Depending on the body water amount, the path width for passing the electricity can be determined. The measurement value of the path width is the bioelectrical impedance. According to a principle of measuring body elements based on the bioelectrical impedance, the bioelectrical impedance is measured by applying a weak AC electrical signal of 1 mA having a frequency band of 50 kHz to a human body. Then, the body water amount is calculated based on the bioelectrical impedance. Also, the protein amount and the inorganic matter amount are calculated based on the body water amount, and the body fat amount is calculated based on the protein amount, the inorganic matter amount, and a patient's weight.

Accordingly, FIG. 1 illustrates a conventional method of measuring body fat, with operations of the conventional body fat measuring method will be described with reference to FIG. 1.

In the conventional method of measuring body fat, by using a bioelectrical impedance analysis, is based on the human body being divided into five impedance lumps, as illustrated in FIG. 2, such that four or eight electrodes are used to apply an electrical current into a human body and measure body fat amount. More specifically, as shown in FIG. 1A, an electrical current can be applied to positions 100 and 105 on an arm and leg, respectively, and a corresponding voltage can be detected across positions 110 and 115 of the respective arm and leg. Then, the body fat amount can be obtained by using the relationship of the current to the detected voltage. In addition, fat amounts in other lumps of a human body may be measured. For example, as shown in FIG. 1B, an electrical current can be applied to both arms at respective positions 120 and 125, and a voltage drop across both arms at positions 130 and 135 may be detected. Also, as shown in FIG. 1C, an electrical current can be applied to positions 140 and 145 on a respective arm and leg, and a voltage drop across both legs at positions 150 and 155 may be detected. Further, as shown in FIG. 1D, an electrical current can be applied to positions 160 and 165 on a respective arm and leg, with a voltage drop across a position 170 of the other arm and a position 175 of the other leg may be detected.

According to the conventional method of measuring body fat, as shown in FIG. 2, the body fat measurement is limited to five representative lumps of a human body. Therefore, it cannot be applied to any particular area of a human body, such as an abdominal region, a chest, a shoulder, and a forearm, which have recently been found to be necessary.

SUMMARY OF THE INVENTION

Embodiments of the present invention set forth an apparatus, medium, and method for measuring body fat thickness of a desired portion of a body by applying an electrical current having a variable frequency to the desired portion of the body.

To achieve the above and/or other aspects and advantages, embodiments of the present invention include an apparatus for measuring body fat, including a current generating unit to generate a current having a predetermined range of variable frequency and to apply the current to a desired area on a body, a detector unit to detect a voltage across the desired area in response to the application of the current and to detect a frequency value at which an impedance of the desired area changes based on a relationship between the detected voltage and the variable frequency, and a body fat calculating unit to calculate a body fat thickness based on the detected frequency value.

The current generating unit may include a voltage generating unit to generate a voltage having the predetermined range of variable frequency, a converter unit to convert the generated voltage into a variable frequency current, and a current supply unit to supply the variable frequency current to the desired area.

The detector unit may include a voltage detector to detect a voltage from the desired area, a signal detector to detect an amplitude and phase of the detected voltage, and a frequency detector to detect a frequency value at which the impedance of the desired area changes, based on a variation of the amplitude and the phase depending on a variation of the frequency.

Further, the frequency detector may include an admittance calculating unit to calculate a susceptance and conductance of the desired area based on the amplitude and the phase, and an impedance-altering frequency detector to detect the frequency value at which the impedance of the desired area changes, based on a variation of the susceptance and the conductance depending the variation of the frequency. The impedance-altering frequency detector may include an inflection point detector to detect an inflection point in a curve passing through a set of points corresponding to detected susceptance and conductance values with respect to the variable frequency, and an inflection frequency detector to detect a frequency value corresponding to a susceptance and the conductance of the detected inflection point.

In addition, the impedance-altering frequency detector may include a first extractor to extract a first equation of a first circle passing through a first set of three points corresponding to detected susceptance and conductance values, for respective first, second, and third frequency values, a second extractor to extract a second equation of a second circle passing through a second set of three points corresponding to detected susceptance and conductance values, for respective fourth, fifth, and sixth frequency values, and a cross point detector to obtain a cross point between the first and second circles and detecting a frequency value corresponding to susceptance and conductance values of the cross point.

The impedance-altering frequency detector may include a circle extractor to extract an equation of a circle passing through a set of three points corresponding to detected susceptance and conductance values, for a respective set of three frequency values, and a minimum frequency detector to detect a minimum frequency corresponding to susceptance and conductance values which do not satisfy the extracted equation of the circle from the variable frequency.

To achieve the above and/or other aspects and advantages, embodiments of the present invention include a method of measuring body fat, including generating a current having a predetermined range of variable frequency and applying the variable frequency current to a desired area on a body, detecting a voltage across the desired area in response to the applied variable frequency current, detecting an impedance-altering frequency in the desired area based on a relationship between the variable frequency and the detected voltage, and calculating body fat thickness of the desired area based on the impedance-altering frequency.

The generation of the current may include generating a voltage having the predetermined range of the variable frequency, converting the generated voltage into the variable frequency current, and supplying the variable frequency current to the desired area.

The detection of the impedance-altering frequency may include detecting an amplitude and phase of the detected voltage, and detecting the impedance-altering frequency of the desired area based on a variation of the amplitude and the phase depending on the variation of the frequency. The detection of the impedance-altering frequency of the desired area may include calculating susceptance and conductance values of the desired area with respect to the variable frequency based on the detected amplitude and the phase, and detecting the impedance-altering frequency of the desired area based on a variation of the susceptance and conductance values depending on the variation of the frequency.

Further, the detection of the impedance-altering frequency of the desired area may include extracting a curve passing through a set of points corresponding to the susceptance and the conductance values, calculated with respect to the variable frequency, detecting an inflection point on the extracted curve, and detecting the frequency value corresponding to susceptance and conductance values of the detected inflection point.

The detection of the impedance-altering frequency of the desired area may include extracting a first equation of a first circle passing through a first set of three points corresponding to detected susceptance and conductance values, for a respective first set of frequency values, extracting a second equation of a second circle passing through a second set of three points corresponding to detected susceptance and conductance values, for a respective second set of frequency values, calculating a cross point between the first circle and the second circle, and detecting the frequency value corresponding to susceptance and the conductance of the calculated cross point.

The detection of the impedance-altering frequency of the desired area may further include extracting an equation of a circle passing through a set of three points corresponding to detected susceptance and conductance values, for a respective set of frequency values, determining whether susceptance and conductance values detected with respect to a predetermined test frequency satisfy the extracted equation of the circle, and repeating the determination by incrementing the test frequency by a predetermined value until the extracted equation of a circle is not satisfied.

To achieve the above and/or other aspects and advantages, embodiments of the present invention include at least one medium including computer readable code to implement embodiments of the present invention.

Additional aspects and/or advantages of the invention will be set forth in part in the description which follows and, in part, will be apparent from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE PREFERRED EMBODIMENTS

Figure 1A:
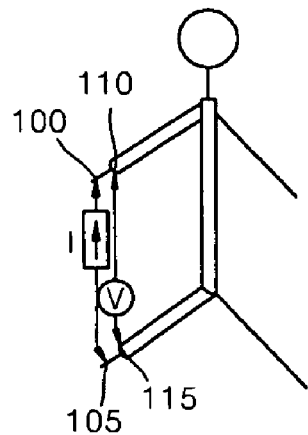
FIGS. 1A-1D illustrate conventional methods for measuring body fat.
Figure 1B:
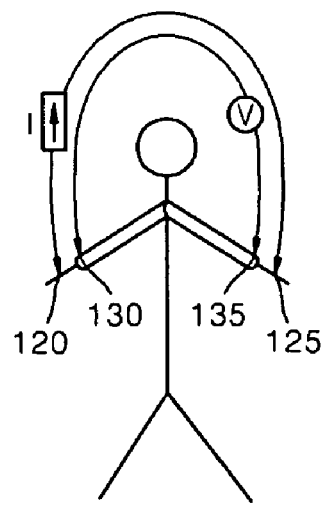
Figure 1C:
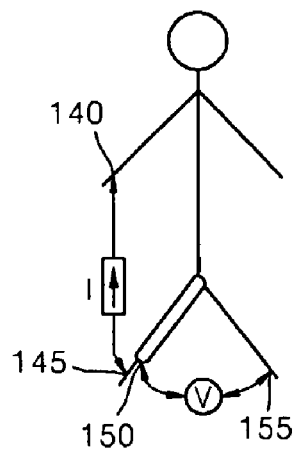
Figure 1D:
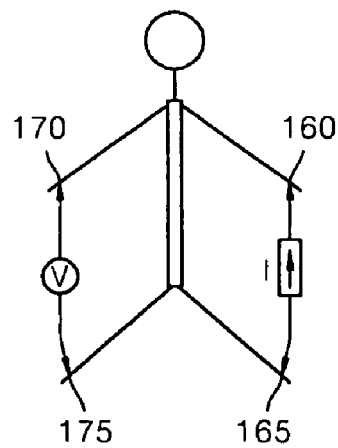
Figure 2:
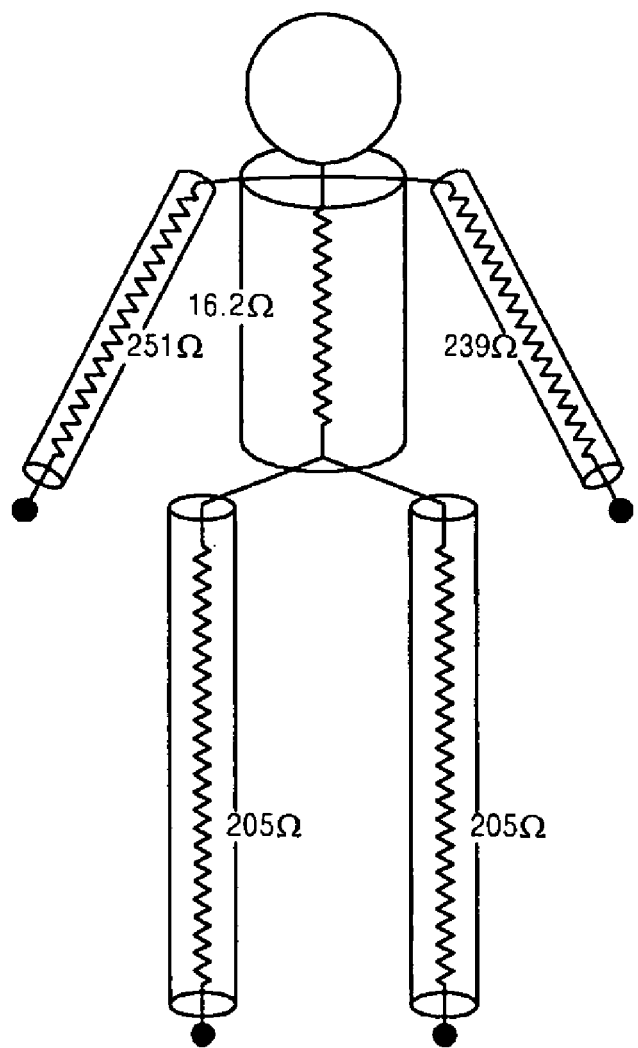
FIG. 2 illustrates a human body divided into five lumps.

Reference will now be made in detail to embodiments of the present invention, examples of which are illustrated in the accompanying drawings, wherein like reference numerals refer to the like elements throughout. Embodiments are described below to explain the present invention by referring to the figures.

Figure 3:
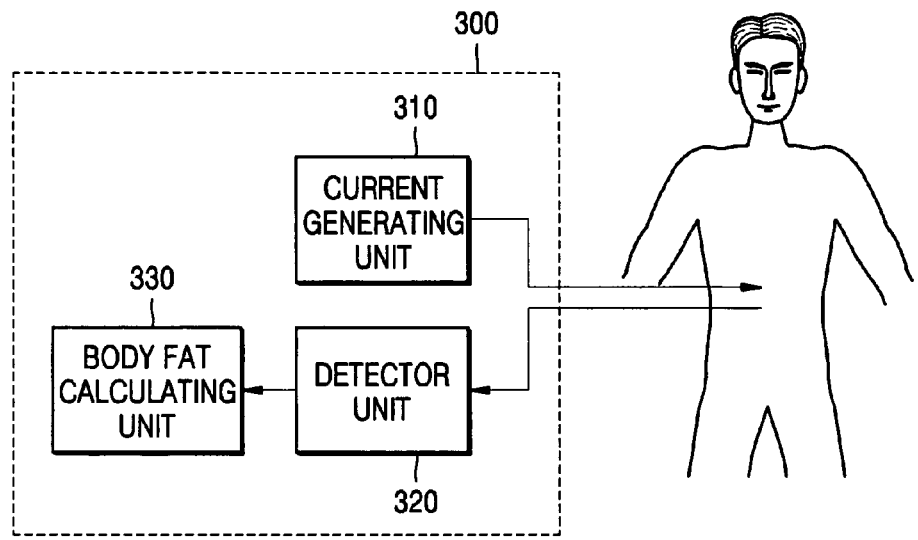
FIG. 3 illustrates an apparatus for measuring body fat, according to an embodiment of the present invention.
Figure 12:
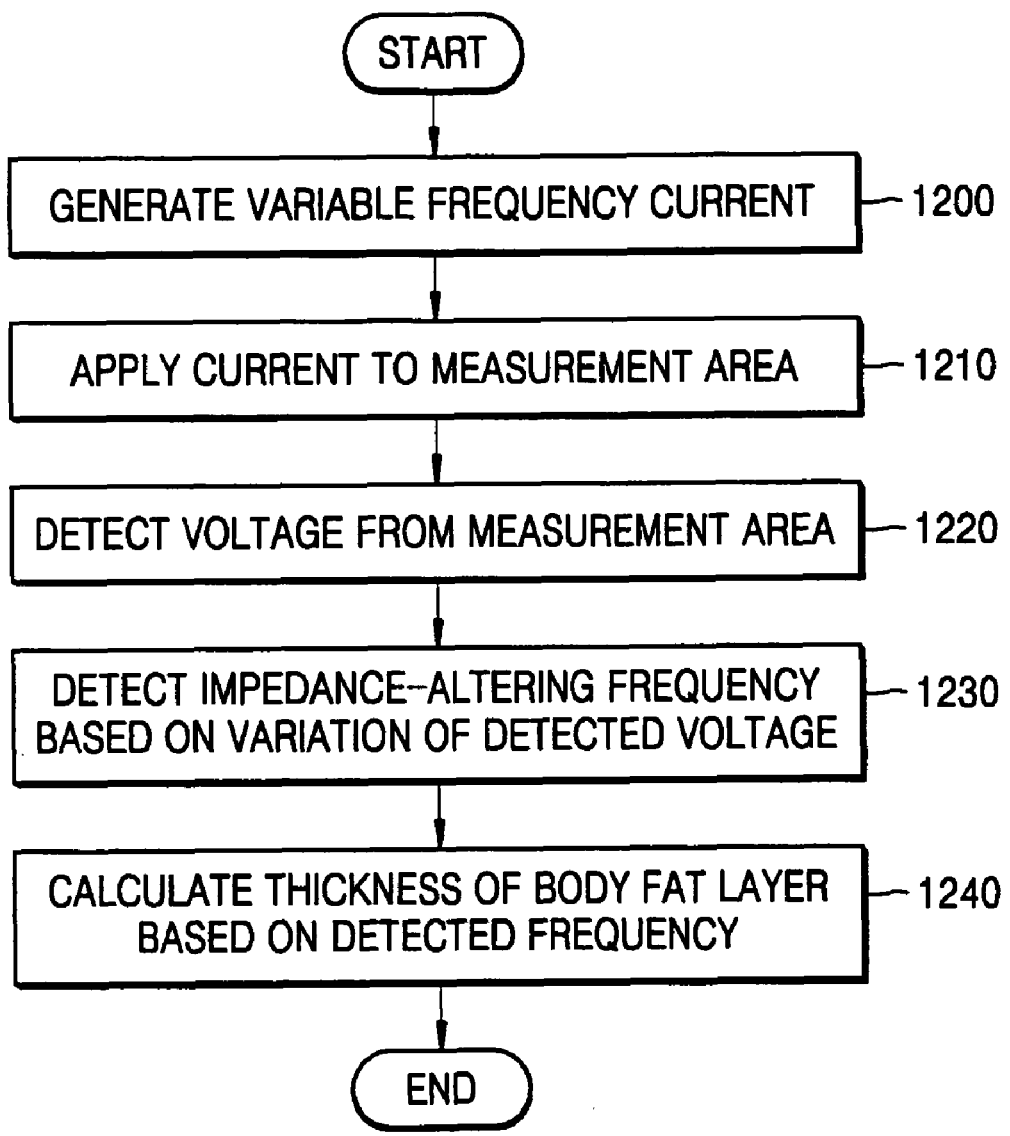
FIG. 12 is a flowchart illustrating a method of measuring body fat, according to an embodiment of the present invention.

FIG. 3 illustrates an apparatus for measuring body fat, according to an embodiment of the present invention. The apparatus for measuring body fat 300 may include a current generating unit 310, a detector unit 320, and a body fat calculating unit 330. Now, operations of the apparatus for measuring body fat will be described, with additional detail, with concurrent reference to FIG. 12, illustrating a method of measuring body fat.

Figure 4:
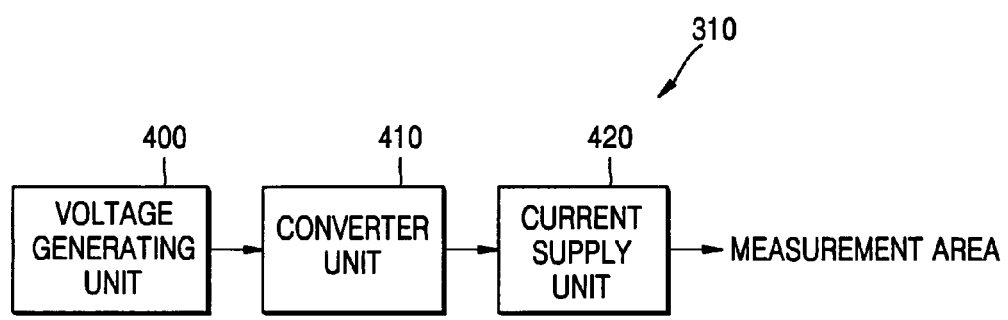
FIG. 4 illustrates a current generating unit, according to an embodiment of the present invention.

The current generating unit 310 can generate an electrical current having a predetermined range of variable frequency (operation 1200), and apply it to a desired area of a human body (operation 1210). The variable frequency may preferably be within a range from several kHz to several GHz. The desired measurement area may include all parts of a human body, for example. FIG. 4 further illustrates a block diagram of the current generating unit 310. The current generating unit 310 can include a voltage generating unit 400, a converter unit 410, and a current supply unit 420. Operations of the current generating unit 310 will now be described with further reference to FIG. 4. The voltage generating unit 400 generates a voltage having a predetermined range of variable frequency, and the converter unit 410 converts the generated voltage into a current having a variable frequency. The current supply unit 420 can supply the converted current having a variable frequency to a measurement area, i.e., a desired area of a human body.

The detector unit 320 detects the voltage generated from the measurement area, in response to the current (operation 1220). Since the current applied from the current generating unit 310 may have a predetermined range of variable frequency, the detector unit 320 can detect voltage variation depending on the variable frequency. Accordingly, impedance of the measurement area can be calculated based on the relationship between the supplied current and the detected voltage. The detector unit 320 can detect the impedance variation in the measurement area depending on the variable frequency based on the variation of the detected voltage depending on the variable frequency. Then, an impedance-altering frequency, i.e., a frequency of the supplied current at which impedance is changed, is detected (operation 1230).

The body fat calculating unit 330 can receive the impedance-altering frequency from the detector unit 320, and calculate body fat thickness of the measurement area based on the relationship between the impedance-altering frequency and body fat thickness (operation 1240). As the frequency of the supplied current increases, the detected voltage in response to the current is generated from a deeper area in the measurement area. Therefore, the body fat calculating unit 330 can calculate the depth at which impedance abruptly changes in the measurement area based on the impedance-altering frequency by using the aforementioned relation. Since the impedance of muscle is different from that of fat, the depth at which impedance changes can be considered as body fat thickness in the measurement area.

The relationship between the frequency of the supplied current and the response depth of the detected voltage can be experimentally obtained by applying a current having a variable frequency to a plurality of predefined fat layers having different thicknesses and then detecting voltages in response to the variable frequency current.

Figure 5:
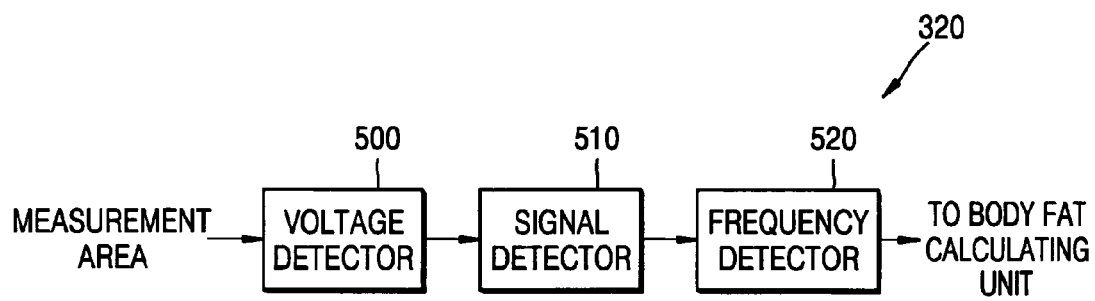
FIG. 5 illustrates a detector unit, such as that of FIG. 3, according to an embodiment of the present invention.
Figure 6:
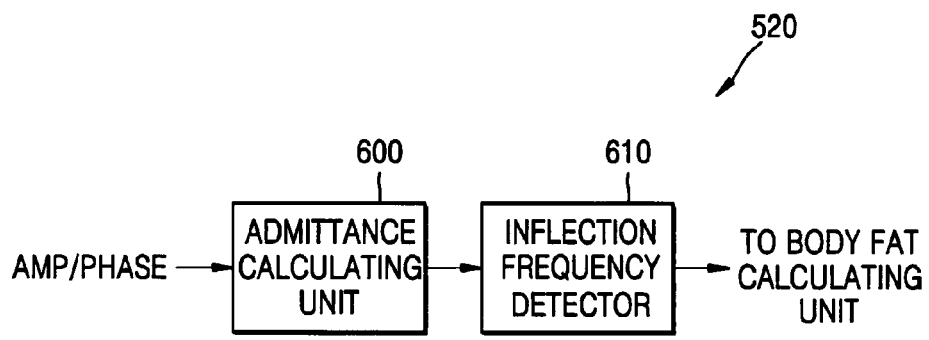
FIG. 6 illustrates a frequency detector of FIG. 5, according to an embodiment of the present invention.
Figure 13:
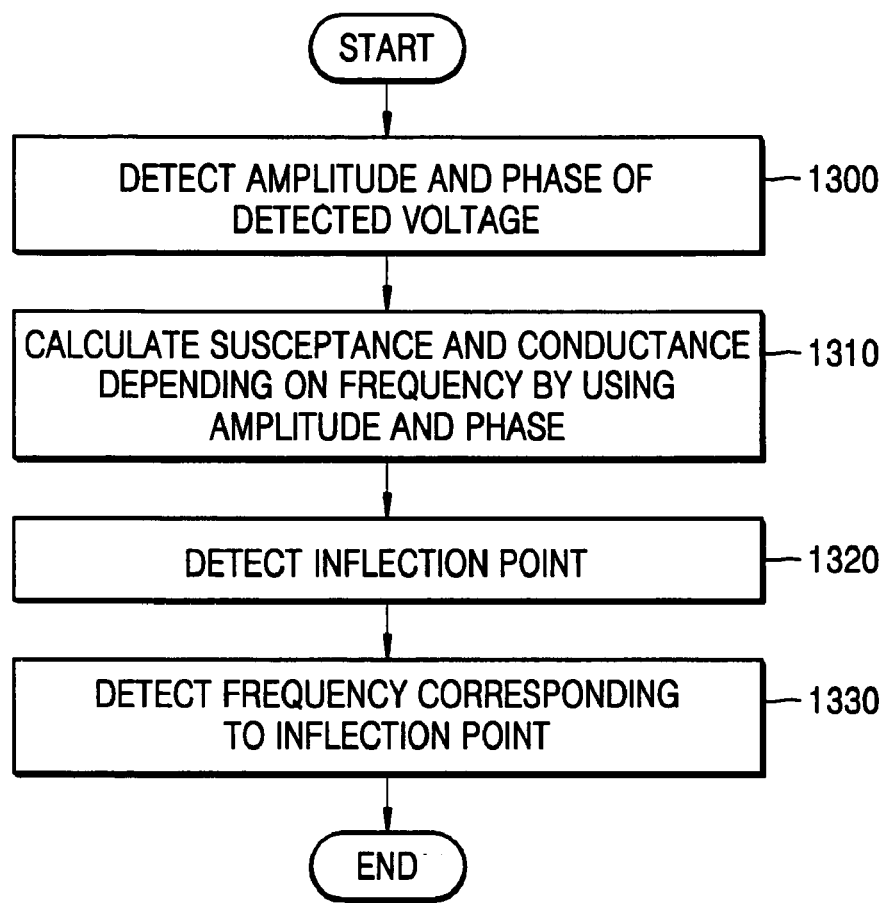
FIG. 13 is a flowchart illustrating an operation 1220 of FIG. 12, according to an embodiment of the present invention.

FIG. 5 illustrates a detector unit, such as that of FIG. 3, according to an embodiment of the present invention. The detector unit can include a voltage detector 500, a signal detector 510, and a frequency detector 520. Operations of the detector unit will now be described concurrently with reference to FIG. 13, which shows a method of detecting an impedance-altering frequency, according to an embodiment of the present invention.

The voltage detector 500 can detect the voltage across the measurement area, in response to the supplied current, of which the frequency is variable in a predetermined range, for example, and the signal detector 510 can detect the amplitude and the phase of the detected voltage (operation 1300).

The frequency detector 520 can calculate admittance, including susceptance and conductance, of the measurement area based on the amplitude and the phase of the detected voltage (operation 1310). Since the frequency of the current supplied from the current generating unit 310 is variable, the frequency detector 520 can extract an inflection point of a curve graphing the variation of admittance depending on variation of the current frequency (operation 1320). Since the detected point of inflection can be considered to be the impedance-altering point, in the measurement area, the frequency detector 520 can detect the impedance-altering frequency by identifying the frequency of the supplied current corresponding to the point of inflection (operation 1330). Now, the relationship between the impedance of the measurement area and the point of inflection in a curve representing admittance variation depending on the frequency variation will be discussed in greater detail with reference to FIGS. 7A-7B and 8.

Figure 7A:
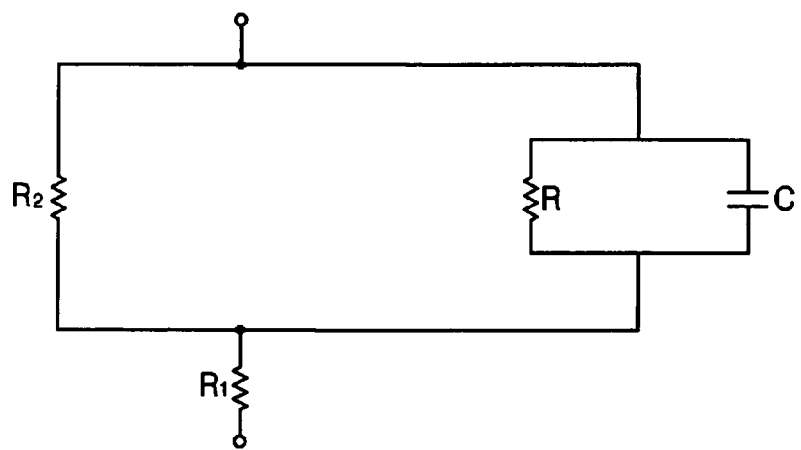
FIG. 7A illustrates a circuit diagram electrically modeling a human skin.

FIG. 7A illustrates a circuit diagram electrically modeling human skin. In the circuit, R and C make up a variable impedance, which represents the impedance of keratin. $R_2$ denotes the resistance of the epidermis, and $R_1$ denotes the resistance of the dermis. The bioelectrical impedance required to measure body fat thickness in a human body is $R_1$, i.e., the impedance of dermis, which is typically located deeper than the keratin or the epidermis.

Figure 7B:
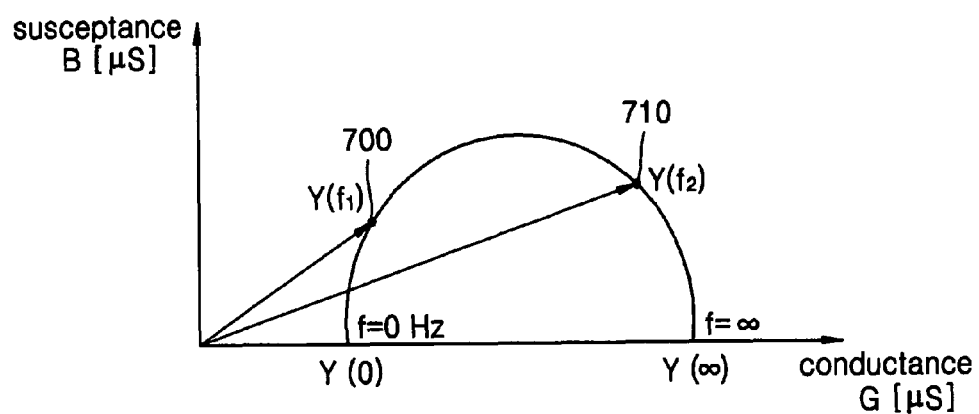
FIG. 7B graphically illustrates a relationship between an admittance of the circuit shown in FIG. 7A and the frequency of the current supplied to the measurement area.

FIG. 7B graphically illustrates the relationship between the admittance of the circuit shown in FIG. 7A and the frequency of the current supplied to the measurement area, where values of $R_1$, $R_2$, R, and C are made to be constant. As shown in FIG. 7B, if the impedance of skin does not vary, the variation of admittance depending on the frequency of the supplied current would be hemispherical when the frequency increases from 0 Hz. Therefore, the admittance 700, when the frequency of the supplied current is $f_1$, and the admittance 710, when the frequency of the supplied current is $f_2$, are located on a hemispherical curve.

Figure 8:
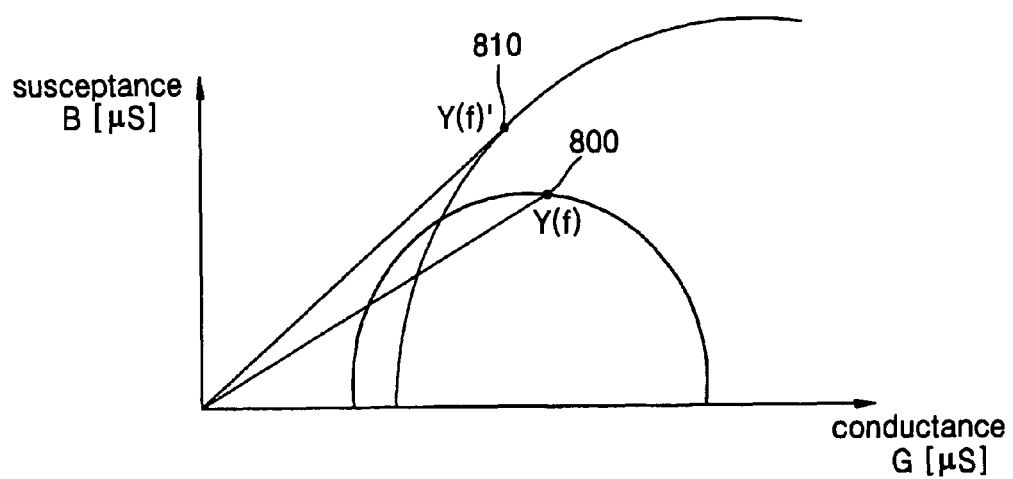
FIG. 8 graphically illustrates variations in an admittance depending on impedance R1 of the modeled skin circuit of FIG. 7A.

FIG. 8 graphically illustrates the variation of admittance depending on the frequency of the supplied current when the impedance R1 of dermis is changed in the circuit shown in FIG. 7A. As shown in FIG. 8, assuming that the frequency of the supplied current is f, as the impedance R1 of dermis increases the admittance location of a skin moves from a point 800 to another point 810, and a radius of a hemispherical curve representing admittance depending on frequency variation becomes larger.

Figure 9A:
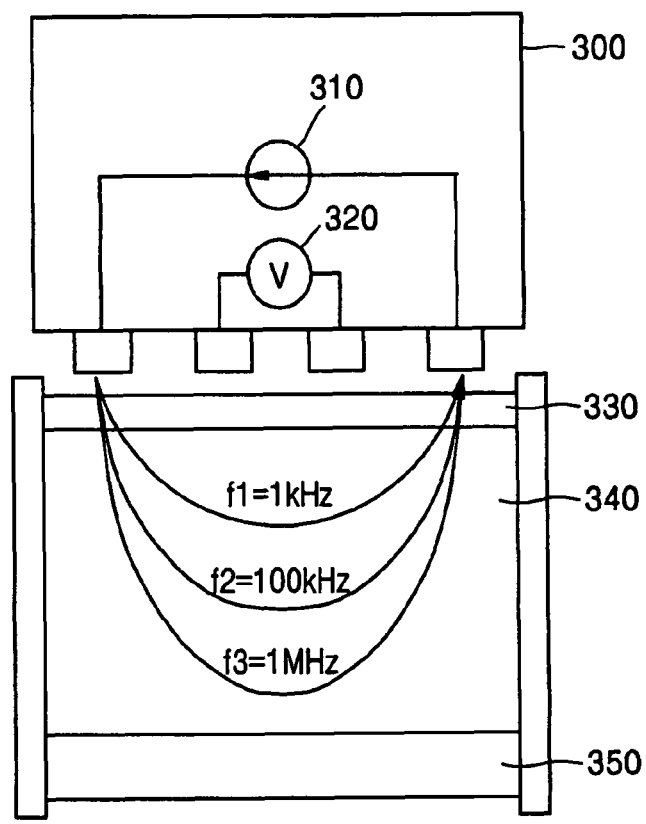
FIGS. 9A-9D illustrate operations of an apparatus for measuring body fat by using a variable frequency current, according to embodiments of the present invention.
Figure 9B:
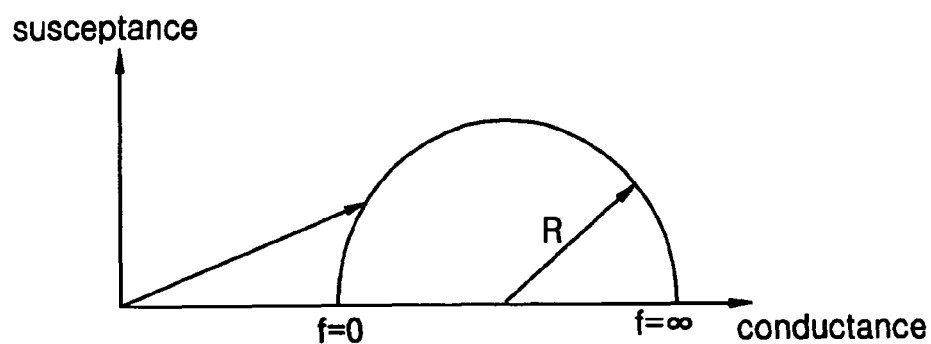
Figure 9C:
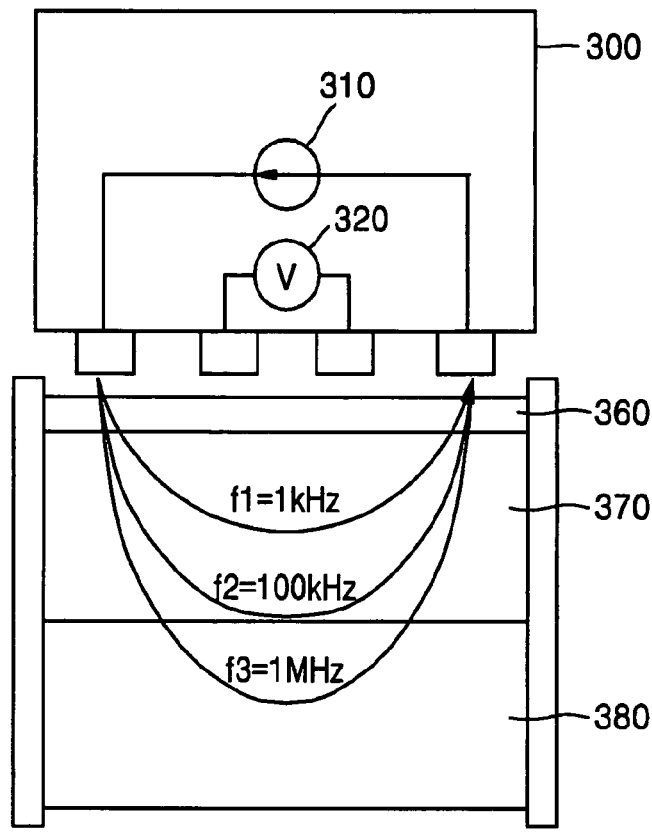

FIGS. 9A-9D illustrate operations of an apparatus for measuring body fat by using a variable frequency current, according to embodiments of the present invention. As illustrated in FIGS. 9A and 9C, the skin is made up of an epidermis layer 330 and 360, a body fat layer 340 and 370, and a muscle layer 350 and 380. In FIGS. 9A-9D, the admittance of skin can be measured by detecting a voltage from the skin as the frequency of the current supplied to the measurement area increases from 1 kHz to 1 MHz. As the frequency of the supplied current increases, the voltage response is generated in deeper skin. Therefore, it is possible to measure admittance of the deepest skin by using the highest frequency (i.e., 1 MHz) of the supplied current.

FIG. 9A illustrates a case that the current is applied to skin having a thick body fat layer, by using an apparatus for measuring body fat, according to an embodiment of the present invention, and FIG. 9B illustrates an admittance curve obtained by using the voltage detected in the skin shown in FIG. 9A. In FIG. 9A, since a skin depth measurable by penetrating a current having a frequency range from 1 kHz to 1 MHz corresponds to a body fat layer 340, it can be recognized that the impedance of the measurement area is constant depending on the frequency variation. Therefore, as shown in FIG. 9B, the admittance curve depending on the frequency variation can be plotted in a hemispherical shape.

Figure 9D:
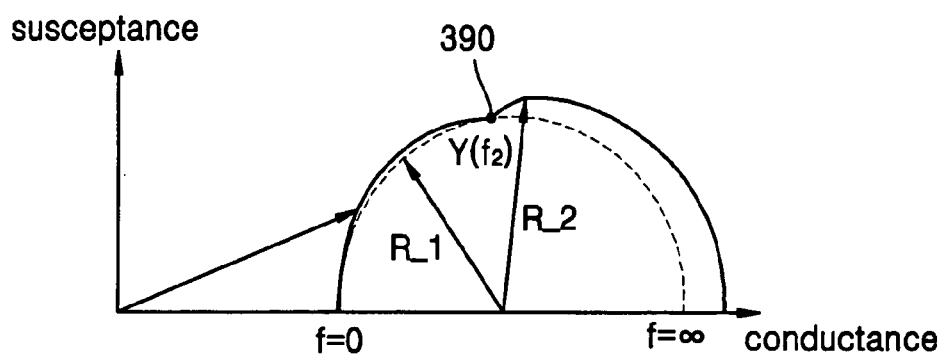

FIG. 9C illustrates the case where the current is applied to skin having a thin body fat layer by using an apparatus for measuring body fat, according to another embodiment of the present invention, and FIG. 9D illustrates an admittance curve obtained by using the voltage detected in the skin shown in FIG. 9C. In FIG. 9C, since a skin depth measurable by penetrating a current having a frequency range from 1 kHz to 100 kMHz corresponds to a body fat layer 370, and a skin depth measurable by penetrating a current having a frequency range from 100 kHz to 1 MHz corresponds to a muscle layer 380, it can be recognized that the admittance curve depending on the frequency variation can be plotted in two hemispheres, due to different impedance values between the body fat layer 370 and the muscle layer 380. Therefore, a point of inflection 390, i.e., a cross point of two hemispheres corresponds to an impedance-altering frequency in the measurement area. As a result, the thickness of the body fat layer 370 can be obtained by detecting the impedance-altering frequency at which the impedance is changed.

Figure 14:
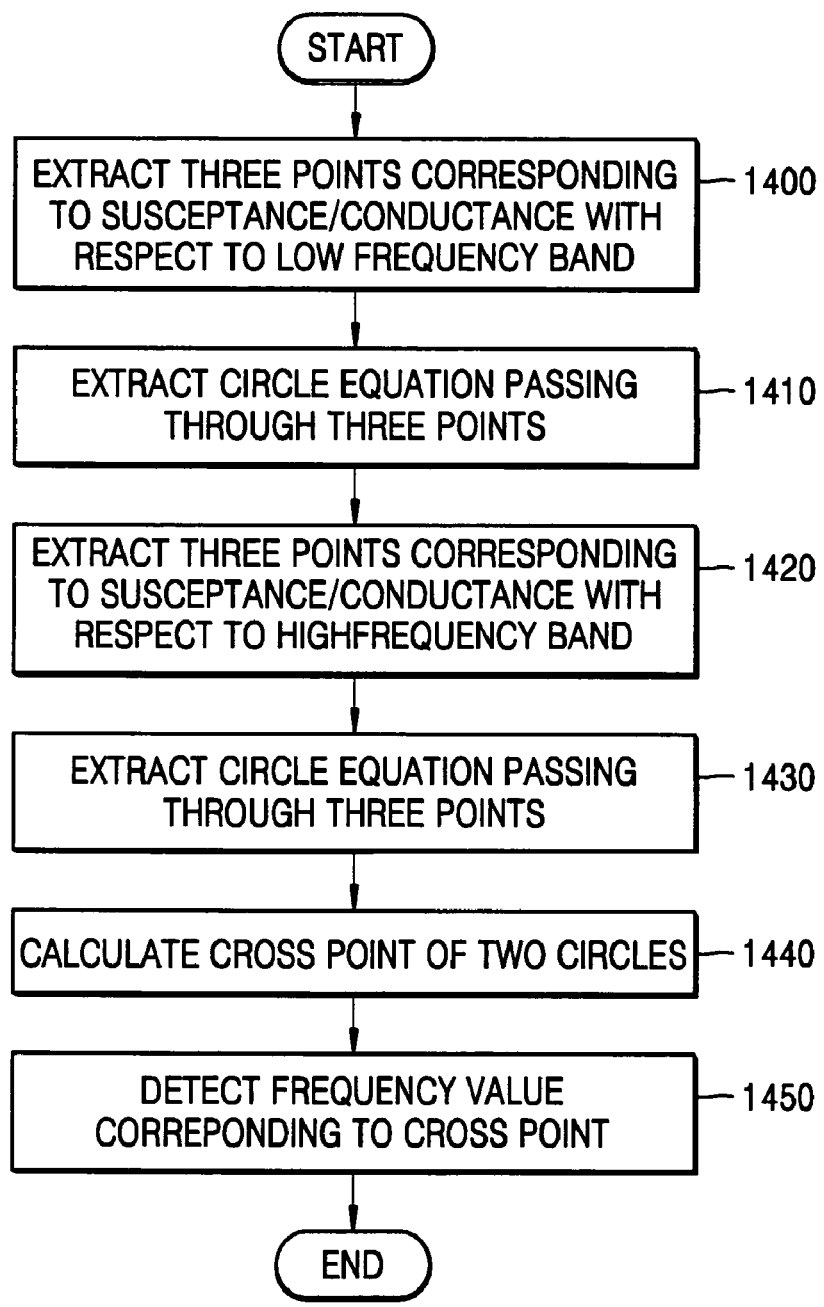
FIG. 14 is a flowchart illustrating a method of detecting an impedance-altering frequency, according to an embodiment of the present invention.

FIG. 14 is a flowchart illustrating a method for detecting a frequency of a supplied current at which impedance of skin changes, according to an embodiment of the present invention. This method of FIG. 14 will also be concurrently described with reference to the graph shown in FIG. 10.

Figure 10:
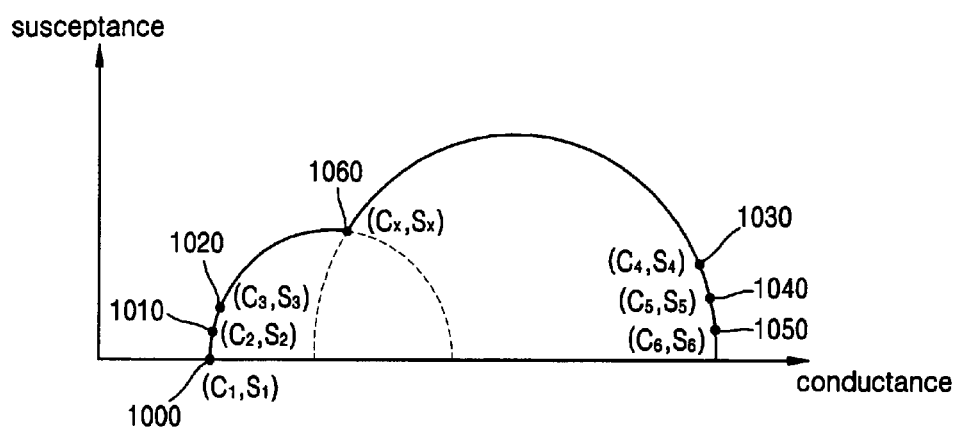
FIG. 10 graphically illustrates a detector operation of FIG. 5, according to an embodiment of the present invention.

As mentioned above, an impedance-altering frequency of the supplied current can be obtained by detecting a point of inflection in an admittance curve depending on frequency variation as shown in FIG. 10. The point of inflection can be obtained by computing equations of two hemispheres making up an admittance curve shown in FIG. 10.

The aforementioned frequency detector 520 can select three frequency values belonging to a low frequency band from the variable frequency range of the supplied current, and extract three points 1000, 1010, 1020 corresponding to admittance values, including susceptance and conductance measured with respect to the three frequency values of the supplied current (operation 1400). The three frequency values may preferably be sufficiently low to measure the admittance of a body fat layer.

The frequency detector 520 can extract a first equation of a first circle passing through the three extracted points 1000, 1010, 1020 (operation 1410).

Subsequently, the frequency detector 520 can select another three frequency values belonging to a high frequency band from the variable frequency range of the supplied current, and extract three points 1030, 1040, 1050 corresponding to admittance values including susceptance and conductance measured for the three frequency values of the supplied current (operation 1420). The three frequency values may preferable be sufficiently high to measure the admittance of a muscle layer.

The frequency detector 520 can extract a second equation of a second circle passing through the three extracted points 1030, 1040, 1050 (operation 1430).

Then, the frequency detector 520 can calculate a cross point between the first and second circles, detected in operation 1410 and 1430, by using the first and second equations (operation 1440). Thus, a frequency having susceptance and conductance values corresponding to the cross point 1060 can be obtained (operation 1450).

Figure 11:
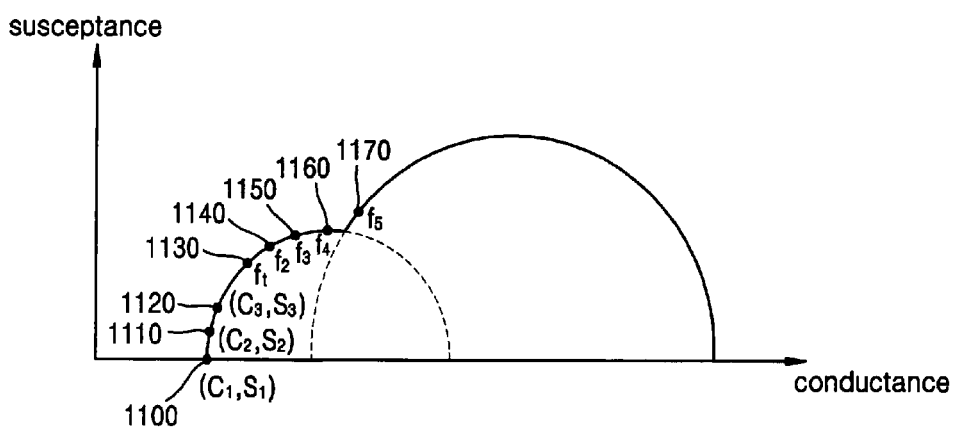
FIG. 11 graphically illustrates another detector for FIG. 5, according to another embodiment of the present invention.
Figure 15:
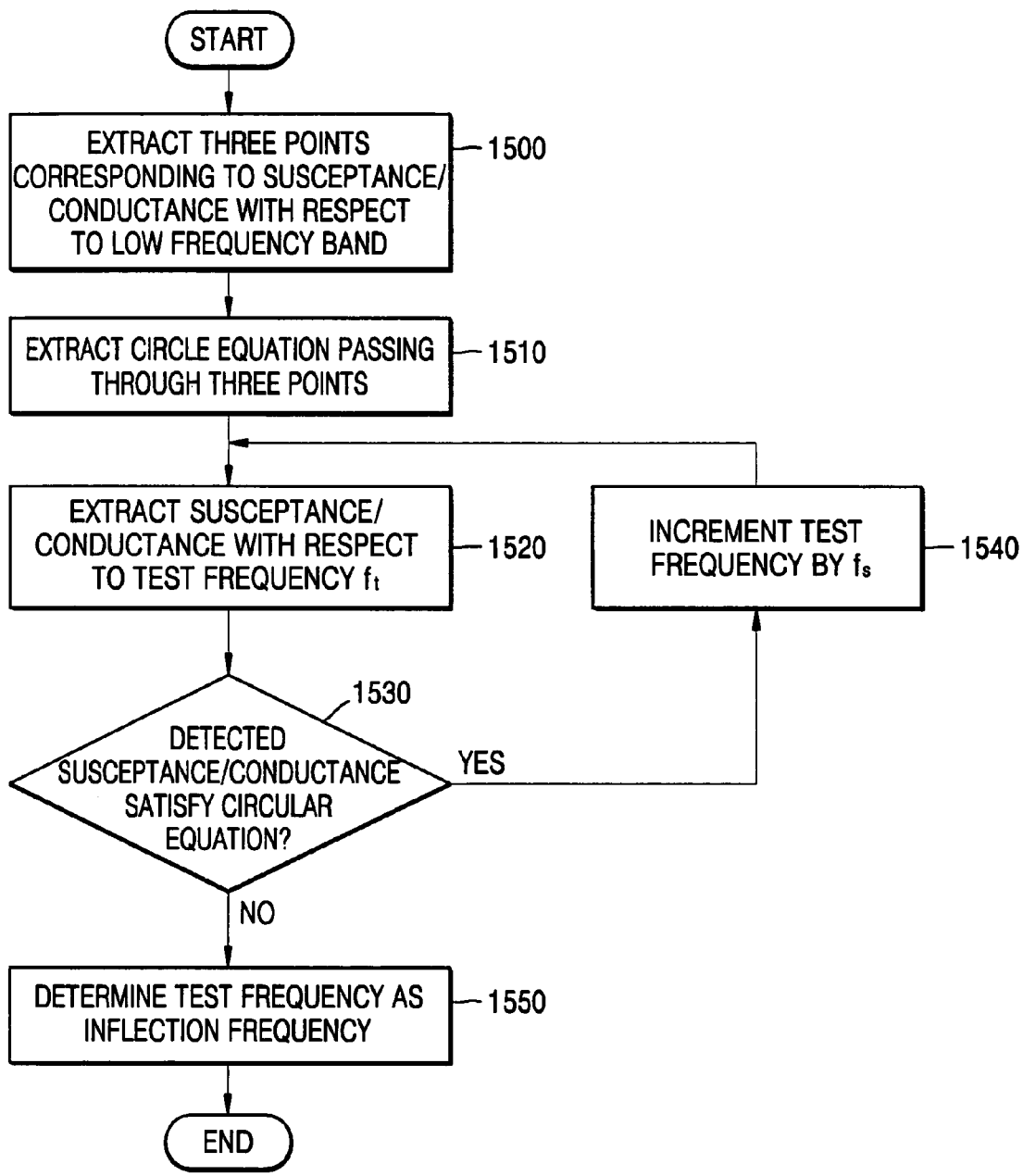
FIG. 15 is another flowchart illustrating a method of detecting an impedance-altering frequency, according to another embodiment of the present invention.

FIG. 15 is a flowchart illustrating a method of detecting a frequency of a supplied current at which impedance of skin changes, according to an embodiment of the present invention. This method will also be concurrently described with reference to the graph shown in FIG. 11.

The frequency detector 520 can select three frequency values belonging to a low frequency band from the variable frequency range of the supplied current, and extract three points 1100, 1110, 1120 corresponding to admittance values, including susceptance and conductance measured for the three frequency values of the supplied current (operation 1500). The preferable three frequency values may be sufficiently low to measure the admittance of a body fat layer.

The frequency detector 520 can extract an equation of a circle passing through the three extracted points 1100, 1110, 1120 (operation 1510).

Unlike the above embodiment, the frequency detector 520 can select a test frequency $f_t$ from the variable frequency range of the supplied current, and also detects a point 1130 corresponding to the susceptance and conductance measured with respect to the test frequency $f_t$ of the supplied current (operation 1520). The test frequency may preferably be sufficiently low to measure the admittance of a body fat layer, but higher than the three frequency values selected in operation 1500.

Then, it can be examined whether or not the susceptance and conductance for the test frequency $f_t$ is located on a circle extracted in operation 1510, i.e., whether it satisfies the equation of a circle (operation 1530). Operation 1520 and 1530 can then be repeated by incrementing the test frequency $f_t$ by a predetermined value $f_s$, e.g., through points 1140-1160 and respective values $f_4$-$f_6$, until the susceptance and the conductance do not satisfy the equation of a circle (operation 1540), e.g., at point 1170 and value $f_7$.

The test frequency at which the susceptance and the conductance do not satisfy the equation of a circle is considered as a frequency corresponding to the point of inflection (operation 1550).

According to embodiments of the present invention, it is possible to measure body fat thickness in any part of a human body by applying a variable frequency current to a desired area. Therefore, health and fatness management can be accomplished for each part of a human body. Also, it is possible to conveniently measure body fat regardless of time and place.

Embodiments of the invention can also be embodied in computer readable code/instructions on a medium, e.g., a computer readable recording medium. The medium may be any data storage/transmission device that can store/transmit data that can be thereafter be read by a computer system. Examples of the media include read-only memory (ROM), random-access memory (RAM), CD-ROMs, magnetic tapes, floppy disks, optical data storage devices, and carrier waves (such as data transmission through the Internet), for example. The medium can also be distributed over network coupled computer systems so that the computer readable code is stored/transferred and implemented in a distributed fashion. Also, functional programs, codes, and code segments for accomplishing the embodiments of the present invention can be easily generated by programmers skilled in the art to which the present invention pertains.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus for measuring body fat, comprising:
    a current generating unit configured to generate a plurality of current signals having different frequencies among a plurality of frequencies varying within a predetermined range, and to apply the generated current signals to a measurement area, the measurement area being a desired area on a body;
    a detecting unit comprising
        a voltage detector configured to detect voltage generated in the measurement area in response to the current signals applied to the measurement area by the current generating unit;
        a signal detector configured to detect amplitudes and phases of the detected voltage; and
        a frequency detector configured to calculate susceptance and conductance of the measurement area based on the detected amplitudes and phases, and to detect an impedance-altering frequency based on a variation of the susceptance and conductance, wherein the impedance-altering frequency is a frequency of the applied current at which impedance is changed and the variation depends on the different frequencies of the current signals corresponding to the detected voltage; and
        a body fat calculating unit configured to calculate a body fat thickness based on the detected impedance-altering frequency.

2. The apparatus of claim 1, wherein the current generating unit comprises:
    a voltage generating unit configured to generate a plurality of voltage signals having different frequencies among the plurality of frequencies varying within the predetermined range;
    a converter unit configured to convert the generated voltage signals into current signals; and
    a current supply unit configured to supply the current signals to the desired area.

3. The apparatus of claim 1, wherein the frequency detector is further configured to detect an inflection point in a curve passing through a set of points corresponding to a variation of admittance depending on variation of the current frequency, and to detect a frequency value corresponding to a susceptance and the conductance of the detected inflection point.

4. The apparatus of claim 1, wherein the frequency detector comprises:
    a first extractor configured to extract a first equation of a first circle passing through a first set of three points corresponding to calculated susceptance and conductance values, for respective first, second, and third frequency values;
    a second extractor configured to extract a second equation of a second circle passing through a second set of three points corresponding to calculated susceptance and conductance values, for respective fourth, fifth, and sixth frequency values; and
    a cross point detector configured to obtain a cross point between the first and second circles and to detected a frequency value corresponding to susceptance and conductance values of the cross point.

5. The apparatus of claim 1, wherein the frequency detector comprises:
    a circle extractor configured to extract an equation of a circle passing through a set of three points corresponding to calculated susceptance and conductance values, for a respective set of three frequency values; and
    a minimum frequency detector configured to detect a minimum frequency corresponding to susceptance and conductance values which do not satisfy the extracted equation of the circle from the variable frequency.

6. A method of measuring body fat, comprising:
    generating a plurality of current signals having different frequencies among a plurality of frequencies varying within a predetermined range and applying the generated current signals to a desired area on a body;
    detecting a plurality of voltage signals across the desired area in response to the applied current signals;
    detecting an impedance of the desired area based on relationship between the supplied current signals and the detected voltage signals,
    detecting an impedance variation in the desired area depending on variable frequency based on the variation of the detected voltage depending on the variable frequency,
    detecting an impedance-altering frequency, the impedance-altering frequency being a frequency of the applied current signal at which impedance is changed, wherein detecting the impedance-altering frequency of the desired area comprises calculating susceptance and conductance values of the desired area based on the detected amplitudes and the phases and detecting the impedance-altering frequency value based on a variation of the susceptance and conductance values, wherein the variation depends on the different frequencies of the current signals corresponding to the detected voltage signals;
    calculating body fat thickness of the desired area based on the detected impedance-altering frequency; and
    outputting the calculated body fat thickness.

7. The method of claim 4, wherein the generation of the current comprises:
    generating a plurality of voltage signals having different frequencies among the plurality of frequencies varying within the predetermined range;
    converting the generated voltage signals into the current signals; and
    supplying the current signals to the desired area.

8. The method of claim 4, wherein the detection of the impedance-altering frequency of the desired area comprises:
    extracting a curve passing through a set of points corresponding to a variation of the susceptance and the conductance values depending on the variation of the current frequency;
    detecting an inflection point on the extracted curve; and
    detecting the frequency value corresponding to susceptance and conductance values of the detected inflection point.

9. The method of claim 6, wherein the detection of the impedance-altering frequency of the desired area comprises:

extracting a first equation of a first circle passing through a first set of three points corresponding to calculated susceptance and conductance values, for a respective first set of frequency values;

extracting a second equation of a second circle passing through a second set of three points corresponding to calculated susceptance and conductance values, for a respective second set of frequency values;

calculating a cross point between the first circle and the second circle; and detecting a frequency value corresponding to susceptance and the conductance values of the calculated cross point.

10. The method of claim 6, wherein the detection of the impedance-altering frequency of the desired area comprises:

extracting an equation of a circle passing through a set of three points corresponding to calculated susceptance and conductance values, for a respective set of frequency values;

determining whether susceptance and conductance values calculated with respect to a predetermined test frequency satisfy the extracted equation of the circle; and repeating the determination by incrementing the test frequency by a predetermined value until the extracted equation of a circle is not satisfied.

* * * * *

UNITED STATES PATENT AND TRADEMARK OFFICE
CERTIFICATE OF CORRECTION

| | | |
|---|---|---|
| PATENT NO. | : 8,103,336 B2 | Page 1 of 1 |
| APPLICATION NO. | : 11/253653 | |
| DATED | : January 24, 2012 | |
| INVENTOR(S) | : Sang-kon Bae et al. | |

It is certified that error appears in the above-identified patent and that said Letters Patent is hereby corrected as shown below:

Column 10, Line 7, In Claim 4, delete "detected" and insert -- detect --, therefor.

Column 10, Line 48, In Claim 7, delete "claim 4," and insert -- claim 6, --, therefor.

Column 10, Line 56, In Claim 8, delete "claim 4," and insert -- claim 6, --, therefor.

Column 11, Line 13, In Claim 9, after "and" delete "the".

Signed and Sealed this
Twenty-ninth Day of May, 2012

David J. Kappos
*Director of the United States Patent and Trademark Office*